(12) United States Patent
Tal (10) Patent No.: US 7,669,601 B2
(45) Date of Patent: Mar. 2, 2010

(54) INTRAUTERINE FALLOPIAN TUBE OCCLUSION DEVICE AND METHOD FOR USE

(76) Inventor: Michael G. Tal, 123 Peck Hill Rd., Woodbridge, CT (US) 06525

( * ) Notice: Subject to any disclaimer, the term of this patent is extended or adjusted under 35 U.S.C. 154(b) by 73 days.

(21) Appl. No.: 11/884,027

(22) PCT Filed: Feb. 15, 2006

(86) PCT No.: PCT/US2006/005245

§ 371 (c)(1),
(2), (4) Date: Aug. 9, 2007

(87) PCT Pub. No.: WO2006/088909

PCT Pub. Date: Aug. 24, 2006

(65) Prior Publication Data

US 2008/0178889 A1    Jul. 31, 2008

Related U.S. Application Data

(60) Provisional application No. 60/653,743, filed on Feb. 15, 2005.

(51) Int. Cl.
*A61F 6/06* (2006.01)
(52) U.S. Cl. ........................ 128/831; 128/830
(58) Field of Classification Search .......... 128/830–841
See application file for complete search history.

(56) References Cited

U.S. PATENT DOCUMENTS

| | | | |
|---|---|---|---|
| 3,405,711 A | 10/1968 | Bakunin | |
| 3,659,596 A | 5/1972 | Robinson | |
| 3,687,129 A | 8/1972 | Nuwayser | |
| 3,704,704 A | 12/1972 | Gonzales | |
| 3,789,838 A | 2/1974 | Fournier | |
| 3,805,767 A | 4/1974 | Erb | |
| 3,918,443 A | 11/1975 | Vennard et al. | |
| 4,353,363 A | 10/1982 | Sopena Quesada | |
| 4,537,186 A | 8/1985 | Verschoof et al. | |
| 4,612,924 A | 9/1986 | Cimber | |
| 4,628,924 A * | 12/1986 | Cimber | 128/839 |
| 4,932,421 A * | 6/1990 | Kaali et al. | 128/831 |
| 5,095,917 A | 3/1992 | Vancaillie | |
| 5,146,931 A | 9/1992 | Kurz | |
| 5,555,896 A * | 9/1996 | Cimber | 128/830 |
| 5,935,137 A * | 8/1999 | Saadat et al. | 606/135 |
| 6,042,030 A | 3/2000 | Howe et al. | |
| 6,346,102 B1 | 2/2002 | Harrington et al. | |
| 6,705,323 B1 | 3/2004 | Nikolchex et al. | |

(Continued)

*Primary Examiner*—Kim M Lewis
(74) *Attorney, Agent, or Firm*—Welsh & Flaxman LLC (57) ABSTRACT

An occlusion device (10) for actively occluding the orifices (12) of the fallopian tubes (14) using the shape of the uterine cavity (16) as a guide to proper positioning of the occlusion device (10) includes a resilient body (18) including an elongated member (28) having a first end (30) and second end (32), and a first orifice plug (20) secured at first end (30) of the elongated member (28) and a second orifice plug (22) secured at second end (32) of the elongated member (28). The first and second orifice plugs (20, 22) are shaped and dimensioned to seat at the orifices (12) of the fallopian tubes (14) or within the fallopian tubes (14) as the elongated member (28) spreads outwardly with the first end (30) and second end (32) moving apart.

9 Claims, 12 Drawing Sheets

U.S. PATENT DOCUMENTS

| | | |
|---|---|---|
| 2002/0198547 A1 | 12/2002 | Schultz |
| 2003/0066533 A1 | 4/2003 | Loy |
| 2004/0009205 A1 * | 1/2004 | Sawhney .................... 424/423 |
| 2005/0125022 A1 | 6/2005 | Ravikumar et al. |
| 2005/0192616 A1 | 9/2005 | Callister et al. |
| 2008/0302368 A1 | 12/2008 | McGuckin et al. |

* cited by examiner

INTRAUTERINE FALLOPIAN TUBE OCCLUSION DEVICE AND METHOD FOR USE

CROSS REFERENCE TO RELATED APPLICATION

The present application is the National Stage of International Application No. PCT/US2006/005245, filed Feb. 15, 2006, entitled "INTRAUTERINE FALLOPIAN TUBE OCCLUSION DEVICE AND METHOD FOR USE", which claims the benefit of U.S. Provisional Patent Application Ser. No. 60/653,743, filed Feb. 15, 2005, entitled "INTRAUTERINE FALLOPIAN TUBE OCCLUSION DEVICE".

BACKGROUND OF THE INVENTION

1. Field of the Invention

The invention relates to a fallopian tube occlusion device and method for use. More particularly, the invention relates to a fallopian tube occlusion device that uses the unique shape of the uterine cavity to ensure delivery and proper positioning thereof, as well as a method for using the occlusion device.

2. Description of the Prior Art

Several types of intrauterine devices (IUDs) are available and used worldwide. There are inert IUDs, copper IUDs and hormone impregnated IUDs. There is ongoing controversy regarding the mechanisms of action of IUDs in humans. Classically, the view was that the IUD in humans acted predominantly after fertilization to prevent implantation, but evidence has accumulated for some effects before fertilization. As a general rule, the pre-fertilization effects are not enough to prevent fertilization and, therefore, the post-fertization effects are most important. The post-fertilization mechanisms of action of the IUD include slowing or speeding the transport of the early embryo through the fallopian tube, damage to or destruction of the early embryo before it reaches the uterus, and prevention of implantation. This mechanism of action is perceived as an early abortion by some, and prevents many patients from using IUDs as a temporary mode of contraception. Another problem with IUDs is expulsion from the uterus and subsequent unwanted pregnancy. Other potential complications of IUDs are uterine infection, uterine perforation and most important ectopic pregnancy. Ectopic pregnancy is a condition where the embryo has implanted outside of the uterine cavity, usually in the fallopian tube. This condition is also hazardous to the patient and can lead to internal bleeding and severe morbidity and even mortality. This potential complication also deters patients from the use of IUDs.

Another problem affecting many women is endometriosis. One of the proposed mechanisms of endometriosis is flow of the menstrual blood through the fallopian tubes into the peritoneal cavity. This condition usually affects younger patients and permanent tubal ligation or occlusion is not warranted. It is thought that the temporary tubal occlusion might prevent the flow of blood through the fallopian tubes and into the peritoneal cavity and thus might improve the patient's symptoms.

Fallopian tube ligation is usually performed surgically. Transvaginal tubal occlusion has also been described before. There are several methods of tubal ligation and occlusion.

With the foregoing in mind, a need exists for an improved IUD replacing currently marketed IUDs and other methods of contraception, such as, tubal ligation. The present invention allows for use of a device that enables tubal occlusion, either permanent or temporary, based on the unique shape of the uterine cavity. This device has the potential for a reduced rate of tubal pregnancy and, therefore, be used by a larger patient population, including those that adamantly opposed to abortion. The present invention also allows nonsurgical tubal occlusion that can be done as an office procedure and without the need for surgery or the need for visualization of the fallopian tube orifices either radiologically or with a hysteroscope. The present invention also provides a treatment option for women that suffer from endometriosis, an often debilitating disease that commonly affects younger women. The present occlusion device uses radial force and inherent properties in its construction to prevent migration or expulsion of the occlusion device. As such, the present invention may be used with the following procedures: contraception, either permanent or temporary; treatment of endometriosis; and potentially treatment of other causes of abnormal uterine bleeding or pelvic pain.

SUMMARY OF THE INVENTION

It is, therefore, an object of the present invention to provide an occlusion device for actively occluding the orifices of the fallopian tubes using the shape of the uterine cavity as a guide to proper positioning of the occlusion device. The occlusion device includes a resilient body including an elongated member having a first end and second end, and a first orifice plug secured at the first end of the elongated member and a second orifice plug secured at the second end of the elongated member. The first and second orifice plugs are shaped and dimensioned to seat at the orifices of the fallopian tubes or within the fallopian tubes as the elongated member spreads outwardly with the first end and second end moving apart.

It is also an object of the present invention to provide method for occluding the fallopian tubes. The method is achieved by delivery an occlusion device into the uterine cavity through the vagina and cervix. The occlusion device includes a resilient body having an elongated member with a first end and second end, and a first orifice plug secured at the first end of the elongated member and a second orifice plug secured at the second end of the elongated member. The first and second orifice plugs are shaped and dimensioned to seat at the orifices of the fallopian tubes or within the fallopian tubes as the elongated member spreads outwardly with the first end and second end moving apart. The occlusion device is then released and the first end and the second end of the elongated member are allowed to move apart until the first and second orifice plugs of the occlusion device distally reach the wall of the uterine cavity and seat at the orifices of the fallopian tubes or within the fallopian tubes.

Other objects and advantages of the present invention will become apparent from the following detailed description when viewed in conjunction with the accompanying drawings, which set forth certain embodiments of the invention.

DESCRIPTION OF THE PREFERRED EMBODIMENTS

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as the basis for the claims and as a basis for teaching one skilled in the art how to make and/or use the invention.

Figure 1:
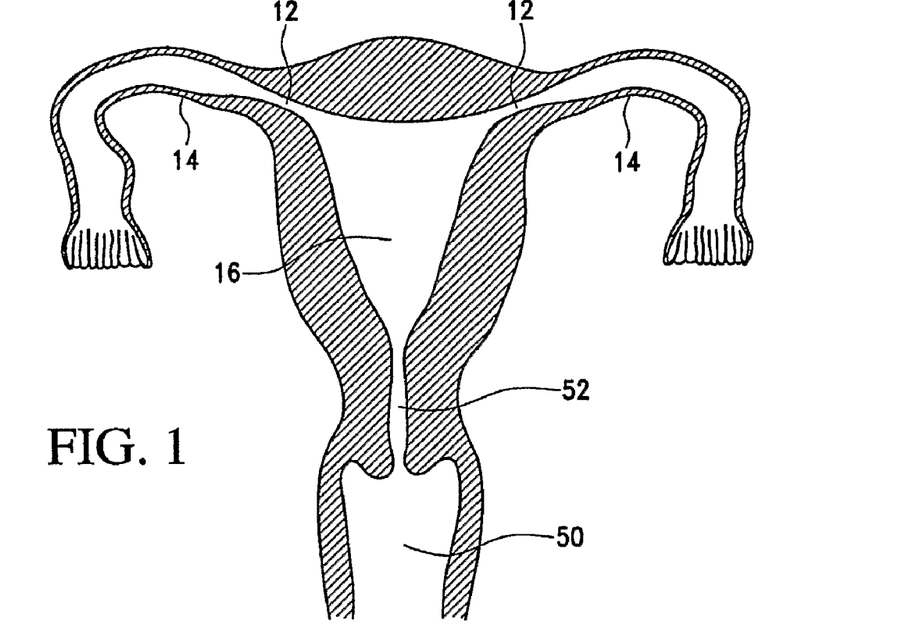
FIGS. 1 to 6 are various views showing delivery of the present occlusion device.

With reference to the various figures, an occlusion device 10 in accordance with a preferred embodiment of the present invention is disclosed that will actively occlude the orifices 12 of the fallopian tubes 14 using the shape of the uterine cavity 16 as a guide to the proper positioning of the occlusion device 10. The shape of the uterine cavity 16 is illustrated in FIG. 1. The uterine cavity 16 is normally in continuation with the fallopian tubes 14. For fertilization, the sperm migrates from the uterine cavity 16 into the fallopian tube 14. Occlusion of the fallopian tube 14 prevents fertilization by preventing migration of the sperm into the fallopian tube 14. The unique shape of the uterine cavity 16 allows the present occlusion device 10 to be inserted into the uterus for positioning in a manner that occludes entry into the fallopian tubes 14. The unique shape also maintains the occlusion device 10 in place without the need for sutures or any other anchoring mechanism. The present occlusion device 10 is also readily removable and prevents migration of the sperm into the fallopian tube 14, thereby, preventing fertilization. The presence of the occlusion device 10 in the uterine cavity 16 also acts as an IUD, but the occlusion effects will prevent fertilization and not necessitate the destruction of the embryo, which is a potential method of contraception by an IUD. This makes the present occlusion device 10 more acceptable to patients and allows its use in a larger part of the population.

As mentioned above, the present occlusion device 10 functions as both an IUD and an occluding structure for the orifices 12 of the fallopian tubes 14. The present invention also relates to a method and apparatus for trans vaginal implantation and removal of the occlusion device 10.

As is discussed below in greater detail, the present occlusion device 10 is composed of a resilient body 18 with first and second orifice plugs 20, 22 at the respective first and second ends 24, 26 thereof. The resilient body 18 is preferably made from a shaped memory alloy metal (Nitinol) or any other material that will provide constant lateral pressure. The orifice plugs 20, 22 for the fallopian tubes 14 can be made from various materials such as silicon, metal, plastic, mesh or a coil with or without a mesh to be anchored in the tissue, and be impregnated with various medications and compounds. The resilient body 18 and/or occlusion plugs 20, 22 can be either inert, meaning without any medication or substance on them or released from them, or they can be impregnated with any material such as hormones or metal, such as, copper. The orifice plugs 20, 22 can also be covered with any other kind of spermicide or other materials.

The present occlusion device 10 can also serve as a delivery system of any occlusion or other devices to the orifices 12 of the fallopian tubes 14. The occlusion device 10 will utilize the shape of the uterine cavity 16 and conform the first and second orifice plugs 20, 22 in the orifices 12 of the fallopian tubes 14. As briefly mentioned above, the orifice plugs 20, 22 can contain any kind of material or medicine to be delivered into the orifices 12 or the fallopian tubes 14. Once the material or medicine is delivered to the orifices 12 or the fallopian tubes 14, the occlusion device 10 can be removed in the manner discussed below with reference to FIGS. 8 to 13 or the first and second orifice plugs 120, 122 may be separated from the resilient body 118 and left in place within the orifices 12 of the fallopian tubes 14 as discussed below with reference to the embodiment disclosed with reference to FIGS. 18, 19 and 20.

Referring to the various figures, and in accordance with a preferred embodiment of the present invention, the present occlusion device 10 includes a resilient body 18 exhibiting spring-like characteristics having first and second orifice plugs 20, 22 secured at opposite ends thereof. The first and second orifice plugs 20, 22 are shaped and dimensioned to ride up the walls of the uterine cavity 16 until they seat within the orifices 12 of the fallopian tubes 14 or within the fallopian tubes 14 as the resilient body 18 spreads outwardly with the first end 24 and second end 26 thereof moving apart.

More particularly, the resilient body 18 includes an elongated member 28 having a first end 30 and a second end 32. The first end 30 of the elongated member 28 is composed of a first leg 34 and the second end 32 of the elongated member 28 is composed of a second leg 36. The first orifice plug 20 is secured at the distal end of the first end 30 of the elongated member 28 and the second orifice plug 22 is secured at a distal end of the second end 32 of the elongated member 28.

The first leg 34 includes a first end 38 and second end 40, and the second leg 36 includes a first end 42 and second end 44. The first ends 38, 42 of the respective first and second legs 34, 36 are respectively connected, while the second ends 40, 44 of the first and second legs 34, 36 are respectively free and are provided with the respective first and second orifice plugs 20, 22. The first ends 38, 42 of the first and second legs 34, 36 are resiliently coupled in a manner allowing the second ends 40, 44 of the first and second legs 34, 36 to be biased away from each other when not restrained in a manner discussed below in greater detail.

With this in mind, the first leg 34 and the second leg 36 are angularly oriented relative to each other creating an elongated member 28 which is substantially V-shaped when the first leg 34 and the second leg 36 are allowed to move away from each other based upon the outward bias inherent in the connection 37 between the first and second legs 34, 36. The inherent bias in the connection 37 is created through the utilization of spring materials or shape memory materials in the construction of the resilient body 18. In accordance with a preferred embodiment, the first and second legs 34, 36 will form a maximum angle of approximately 150 degrees when entirely unrestrained in a manner preventing them from moving away from each other.

Although a preferred embodiment of the present invention employs a V-shaped elongated member, it is contemplated the elongated member may be formed with a variety of shapes (whether in the two dimensional plane or three dimensional plane) so long as it retains its spring like properties. Examples of contemplated shapes are shown in FIGS. 14a to 14e: FIG.

Figure 14A:
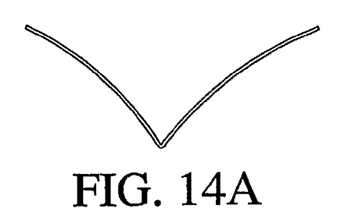
FIGS. 14a to 14e show various shapes which the elongated member of the occlusion device may take in accordance with the present invention.
Figure 14B:
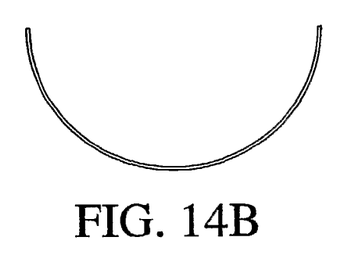
Figure 14C:
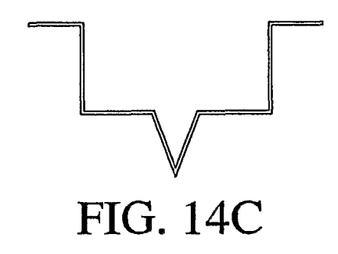
Figure 14D:
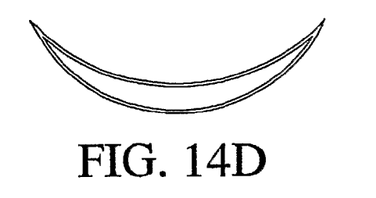
Figure 14E:
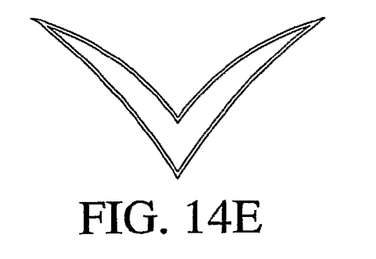

14a shows a V-shaped elongated member; FIG. 14b shows a U-shaped elongated member; FIG. 14c shows a stepped elongated member; FIG. 14d shows a crescent shaped elongated member; and FIG. 14e shows a chevron shaped elongated member.

Considering the various shapes that may be employed in accordance with a preferred embodiment of the present invention, it is contemplated movement, that is, the outward bias of the first and second legs may be achieved by creating resilience along the length of the first and second legs rather than at the connection point of the first and second legs. For example, where the first and second legs are formed of Nitinol, the first and second legs may be formed such that they bow outwardly when exposed to elevated activation temperature upon placement within the body.

With regard to the material construction of the elongated member it may be composed of resilient, biocompatible materials (metal, polymer or composite) or shape memory (or superelastic) alloy materials (for example, Nitinol) capable of offering the outwardly biasing characteristics discussed herein and required for proper operation of the present invention.

Figure 15A:
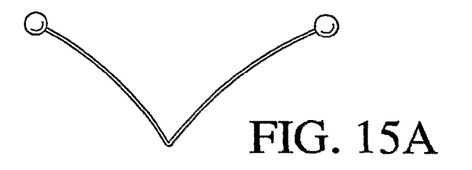
FIGS. 15a to 15f show various shapes which the orifice plugs may take in accordance with the present invention.
Figure 15B:
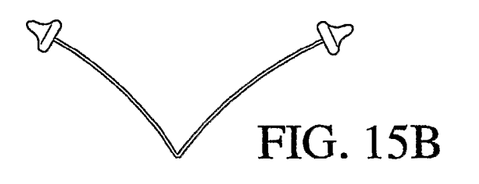
Figure 15C:
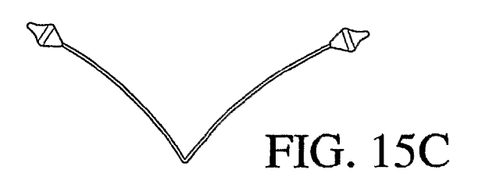
Figure 15D:
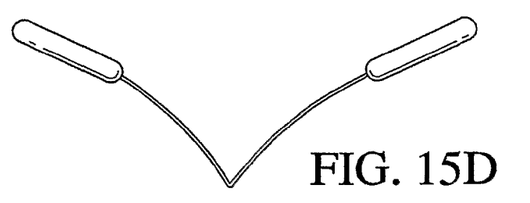
Figure 15E:
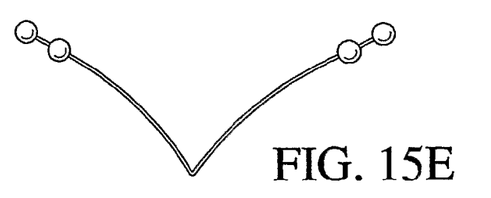
Figure 15F:
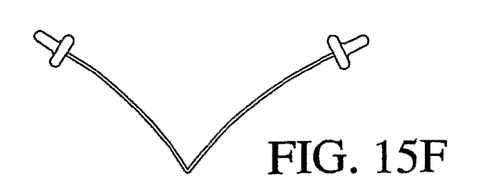

With regard to the orifice plugs, they may also vary substantially. As shown with reference to FIGS. 15a to 15f, the orifice plugs may be spherical (FIG. 15a), conical with a wide concave tip portion (FIG. 15b), conical with a straight tip portion (FIG. 15c), cylindrical (FIG. 15d), spherical will multiple small spheres (FIG. 15e) or conical with a narrow concave tip portion (FIG. 15f). The orifice plugs can be made of silicone, plastic, metal, mesh or any other material with any medication or substance impregnated in it to prevent sperm from entering the fallopian tube. It can also be composed of a coil with or without a mesh to be anchored in the tissue. The shape of the device can also take into consideration the removal process and a special hook or handle for removal might be added.

Figure 2:
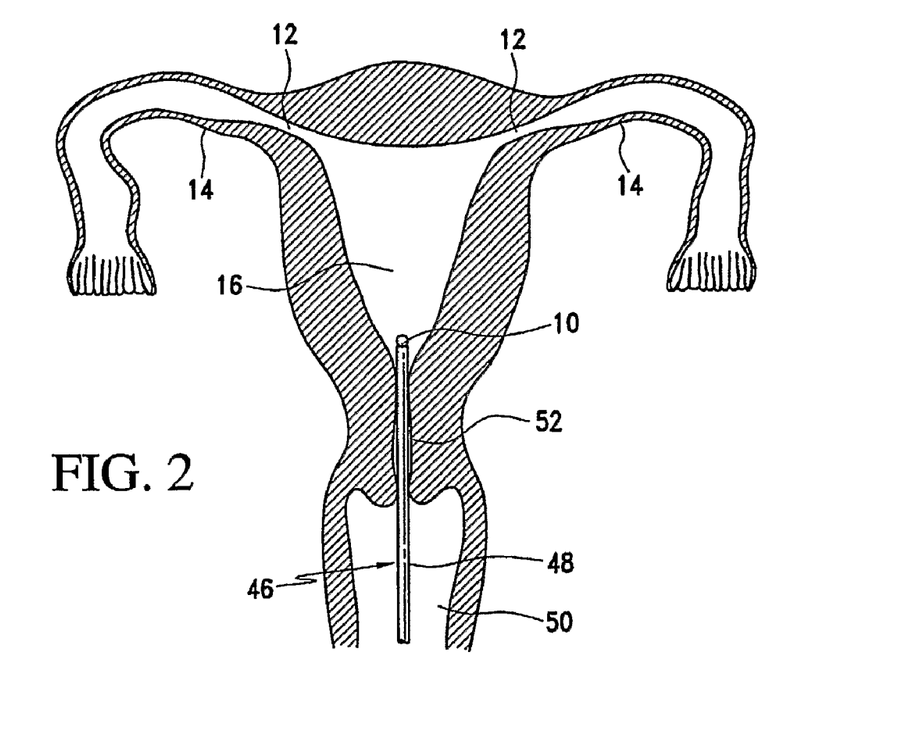
Figure 3:
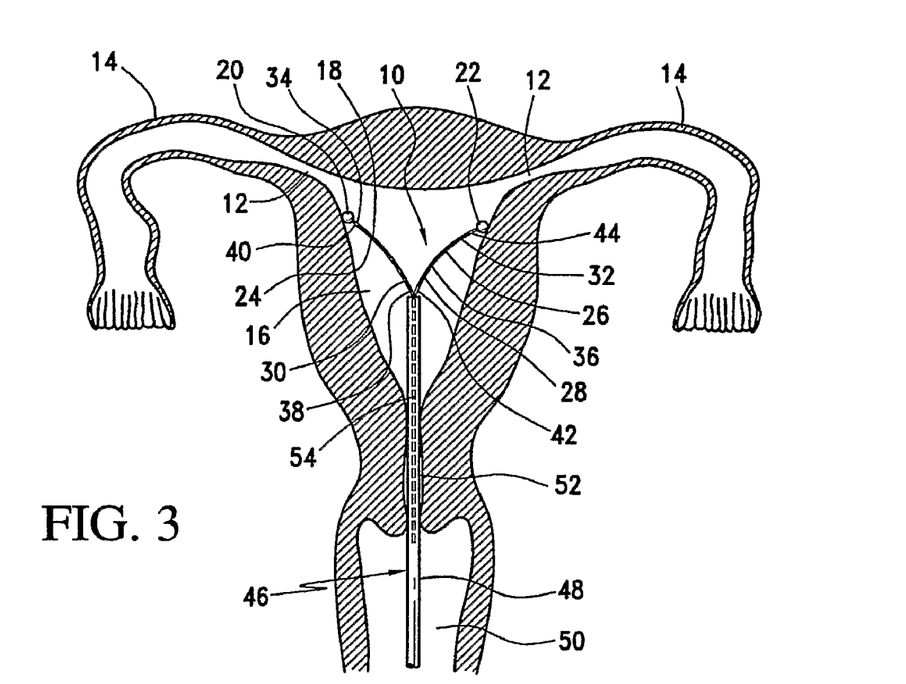
Figure 4:
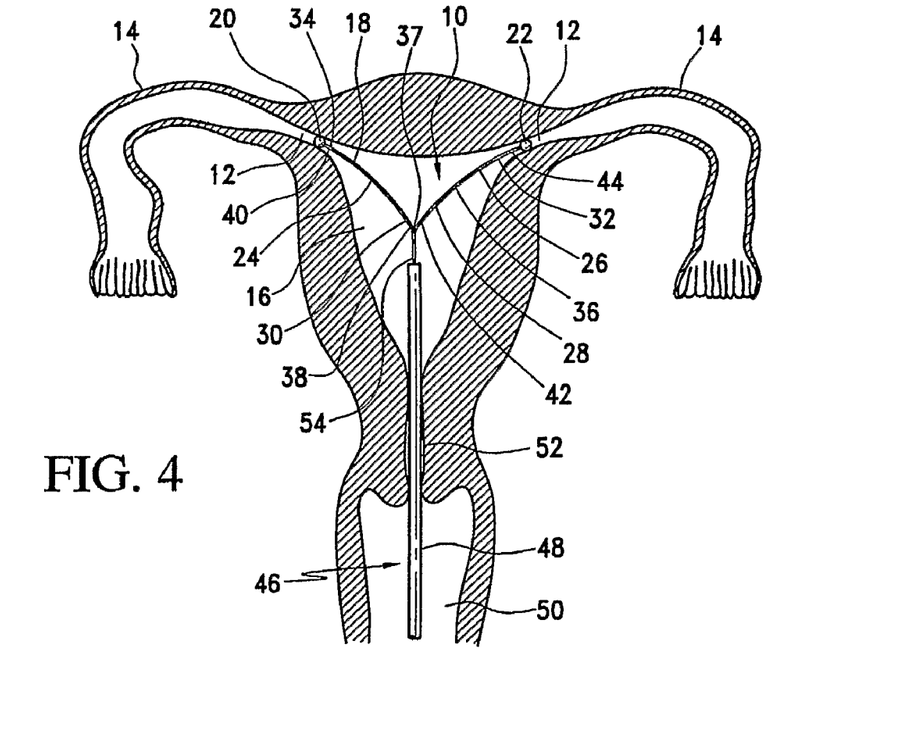
Figure 5:
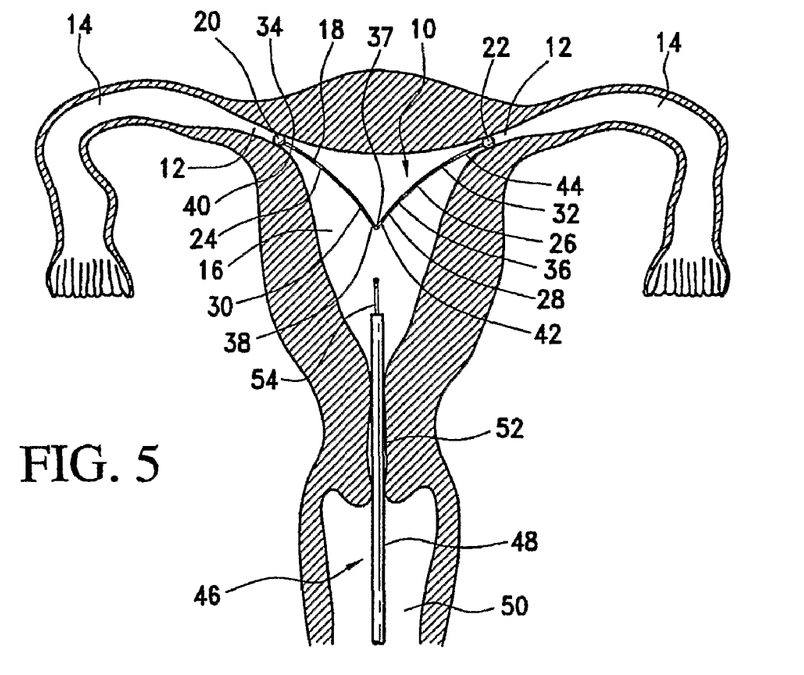
Figure 6:
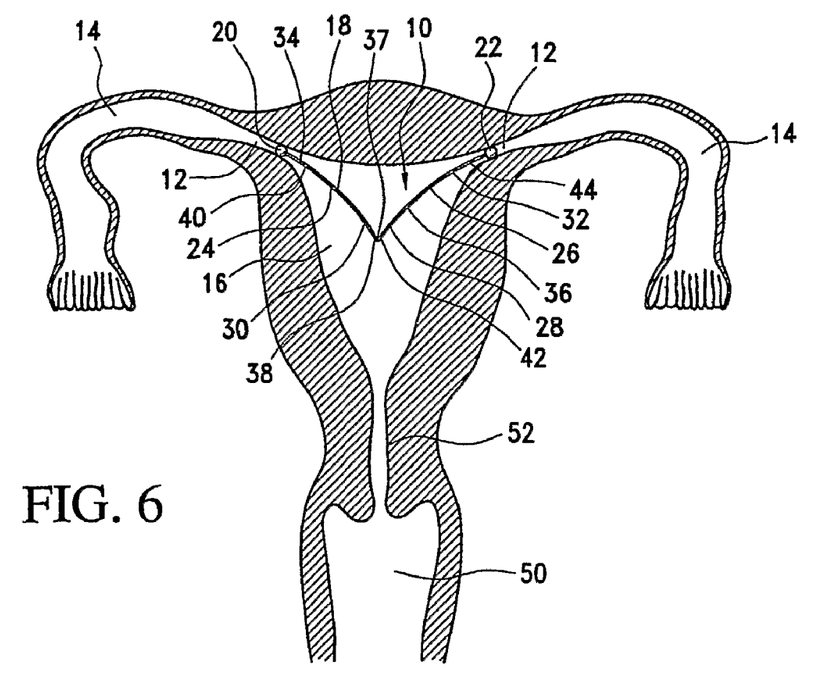
Figure 7A:
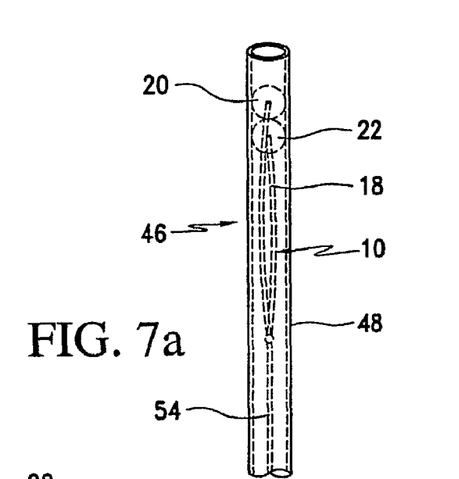
FIGS. 7a to 7d are detailed views showing the delivery apparatus for use in accordance with the present invention with the steps of forcing the occlusion device from within a container via a delivery rod being shown.
Figure 7B:
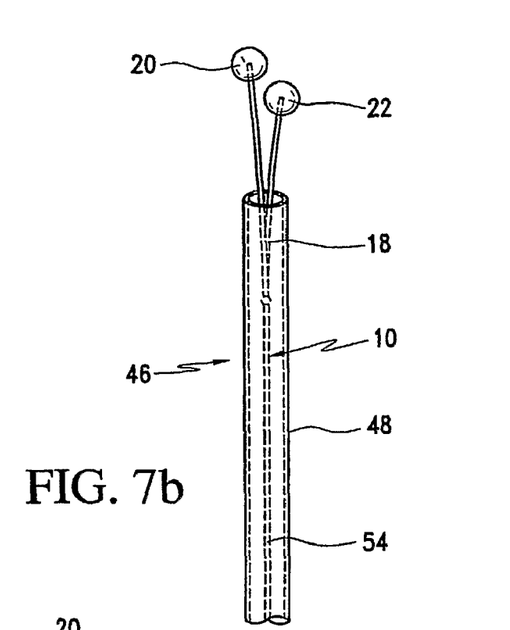
Figure 7C:
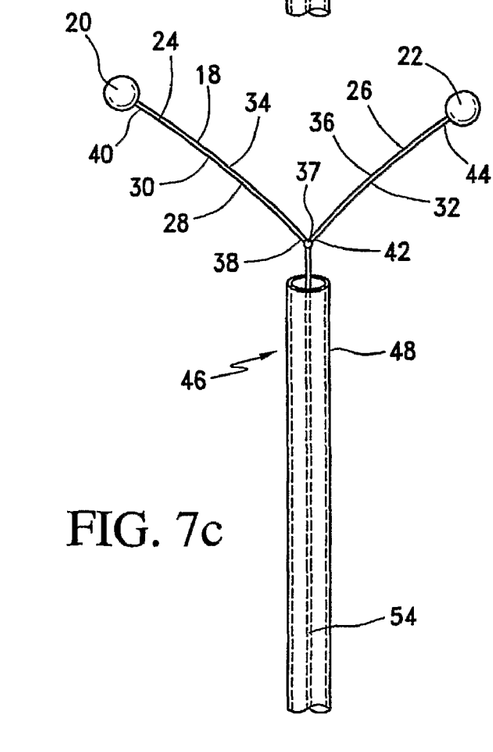
Figure 7D:
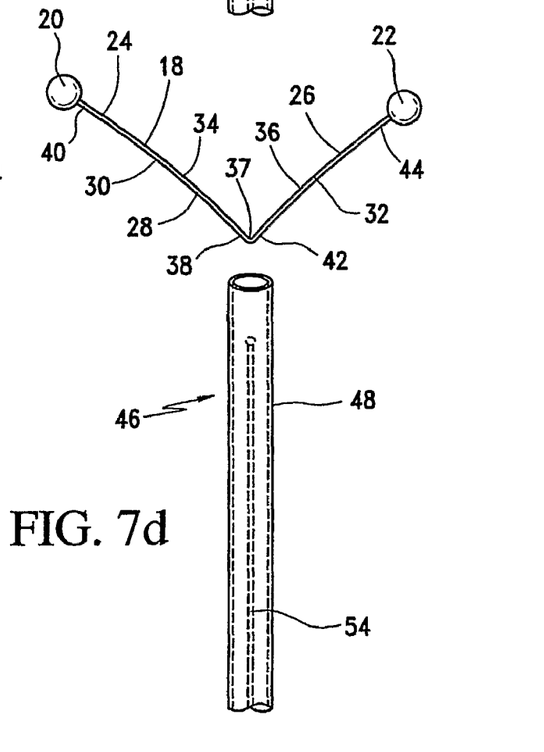
Figure 8:
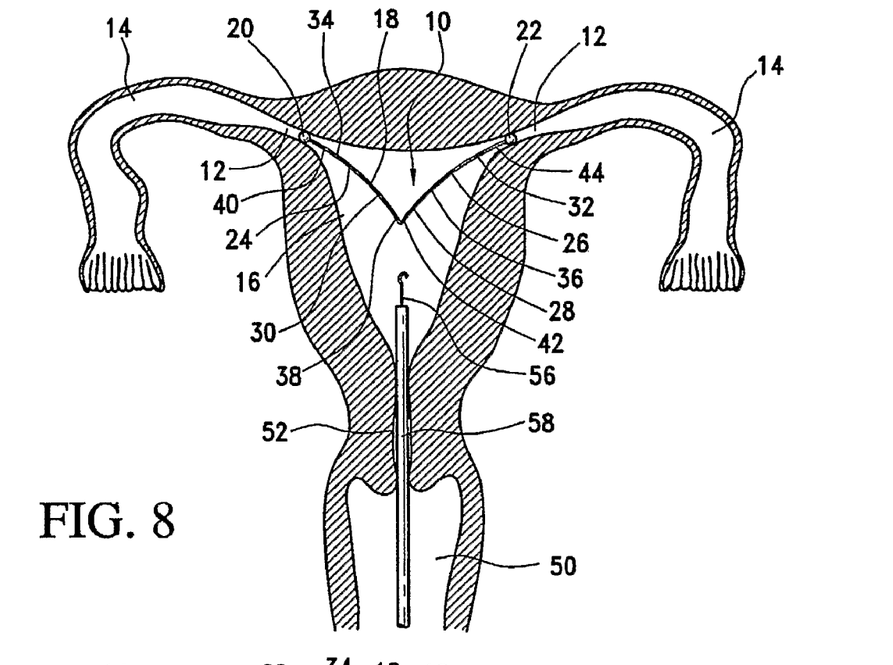
FIGS. 8 to 13 are various views showing retrieval of the present occlusion device.

The present invention also relates to a delivery method and delivery apparatus 46 for the present fallopian occlusion device 10. In accordance with a preferred embodiment of the present invention, the occlusion device 10 is packaged in a small caliber longitudinal container 48. This container 48 is advanced into the uterine cavity 16 through the vagina 50 and cervix 52 (FIG. 2). Once inside the uterine cavity 16, the occlusion device 10 is partially released and advanced from the delivery container 48 via a delivery rod 54 extending through the container 48 for pushing the occlusion device 10 from its storage positioned within the container 48, preferably, while pulling the container (or sheath) 48 back so as to prevent damage to the uterus or device. This releases the present occlusion device 10 from within the container 48 and allows the occlusion device 10 (with the delivery rod 54 secured thereto) to take a shape of a "Y" (FIG. 3). The occlusion device is further advanced within the uterine cavity 16. As the occlusion device 10 opens with the first and second legs 34, 36 moving apart, the orifice plugs 20, 22 of the occlusion device 10 distally reach the back wall of the uterine cavity 16, and direct themselves to the orifices 12 of the fallopian tubes 14 until they seat at the orifices 12 of the fallopian tubes 14 or within the fallopian tubes 14 (FIG. 4). At that point when the occlusion device 10 can be compressed against the fallopian tube orifices 12 it will be released (FIG. 5), whether manually or automatically, from the delivery apparatus 46. The delivery apparatus 46 will be removed and the present occlusion device 10 will stay in place (FIG. 6).

A proposed embodiment for the delivery apparatus 46 is illustrated in FIGS. 7a to 7d. This illustration shows the delivery apparatus 46 with its orifice plugs 20, 22 arranged longitudinally within the delivery container 48. Because of the need to maintain the delivery container 48 in the lowest profile possible (the bigger the delivery system the more dilatation of the cervix is needed), the orifice plugs 20, 22 are located one if front of the other. This also means that the two "legs" 34, 36 of the occlusion device 10 in this embodiment are a slightly different length.

Figure 9:
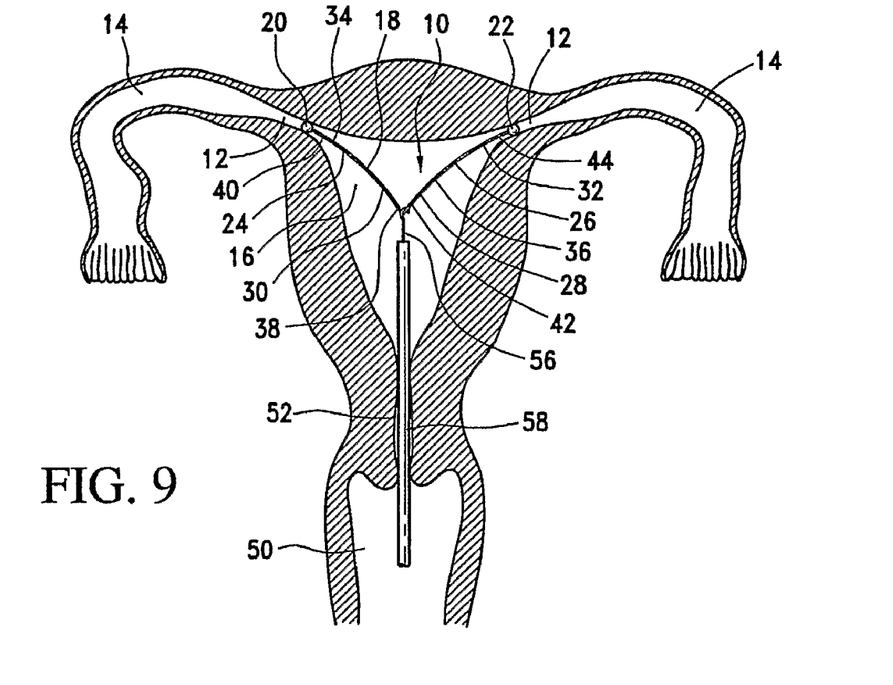
Figure 10:
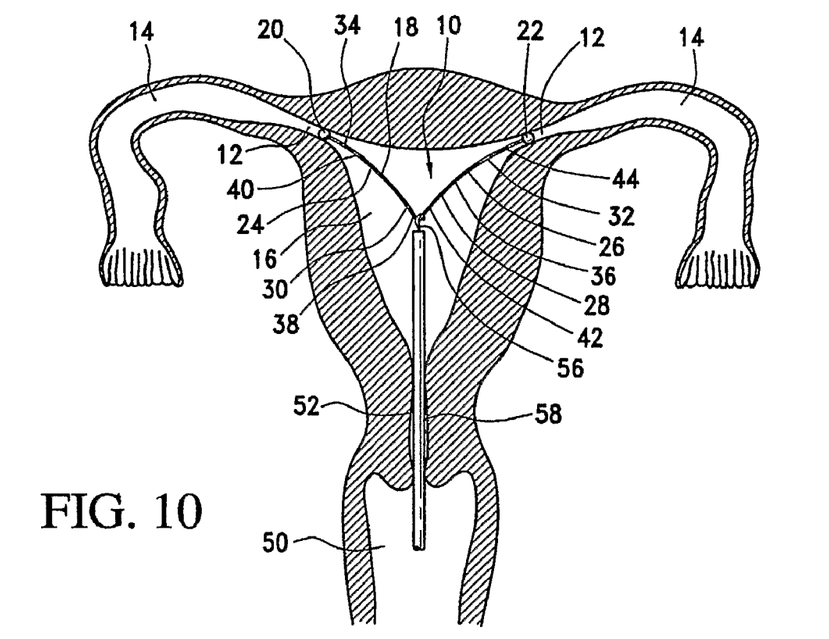
Figure 11:
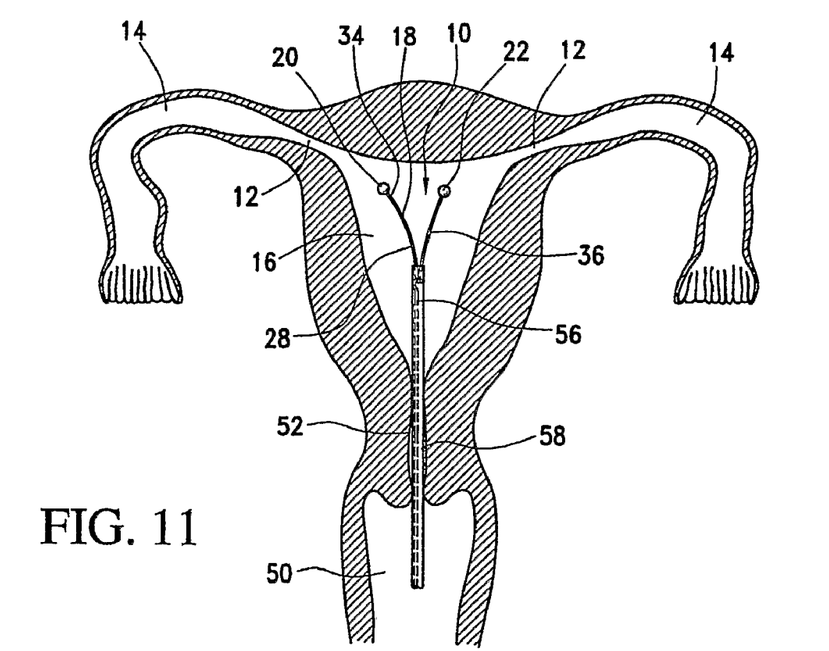
Figure 12:
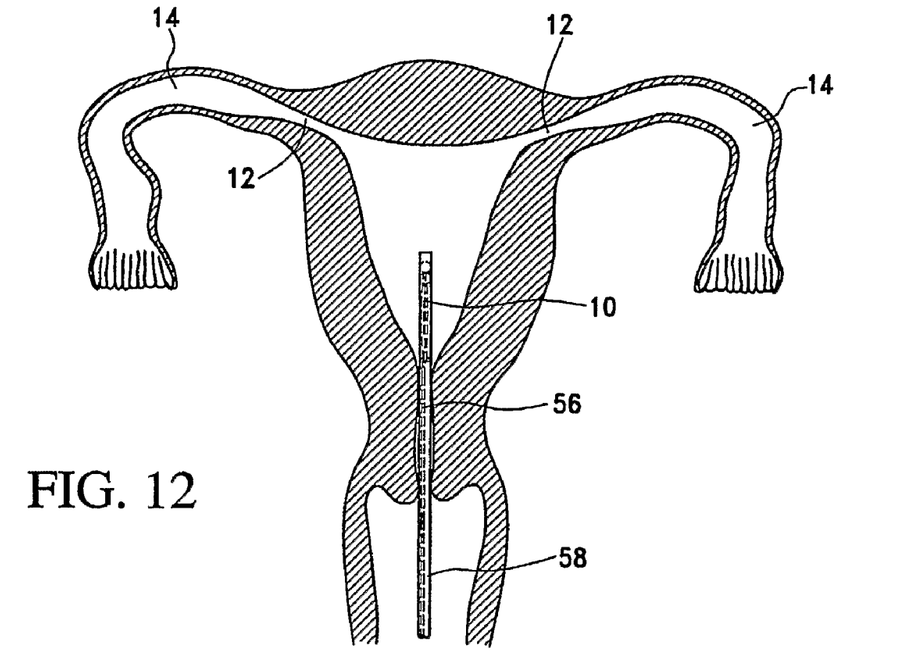
Figure 13:
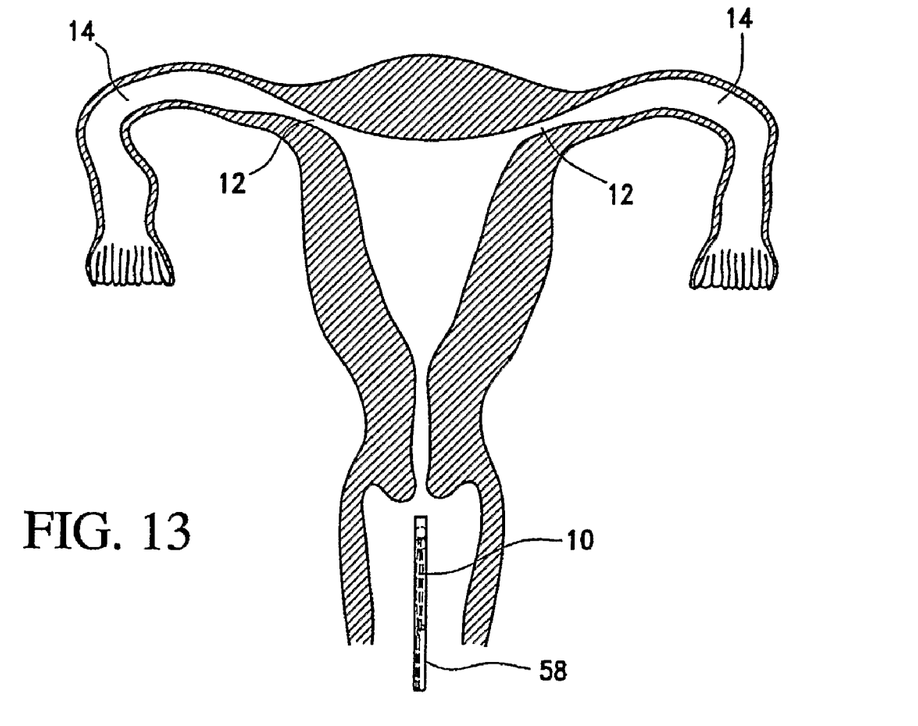

Once delivered and properly positioned, the present occlusion device 10 can stay for years in the uterine cavity. When removal of the occlusion device 10 is desired, a hook 56, or other removal apparatus that engages the device, will be advanced through the vagina 50 and cervix 52 (FIG. 8) and the connection point (for example, a metallic spring) between the orifice plugs 20, 22 and the first and second legs 34, 36 will be grasped (FIG. 9). The hook 56 will pull on the occlusion device 10 and insert it into a sheath 58 or into the hysteroscope (FIG. 10, 11, 12). At that stage, the contained occlusion device 10 is removed from uterus and out through the cervix 52 and vagina 50 (FIG. 13). This removal would be done either with or without direct visualization or under fluoroscopic guidance.

Figure 16:
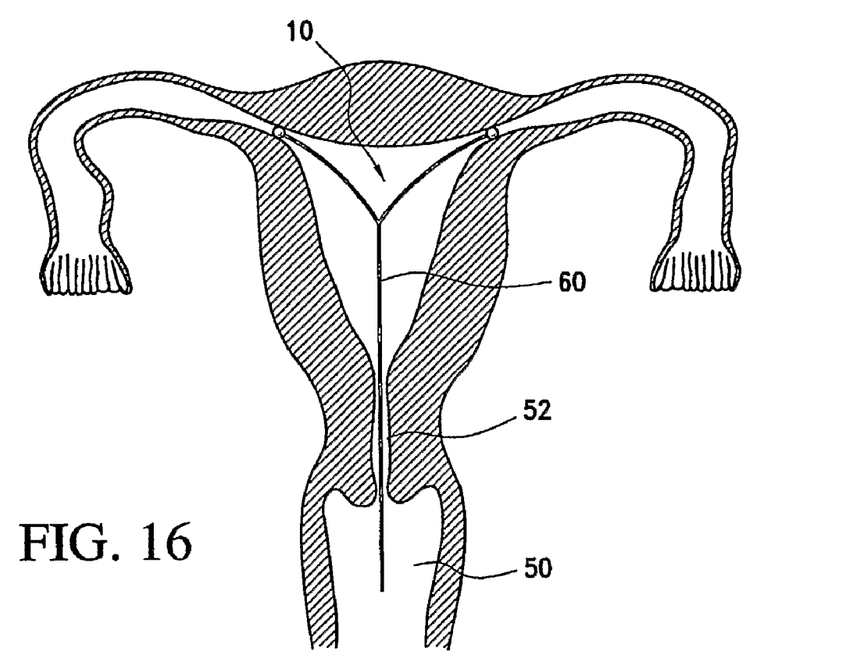
FIGS. 16 and 17 show alternate embodiments for retrieval of the occlusion device.
Figure 17:
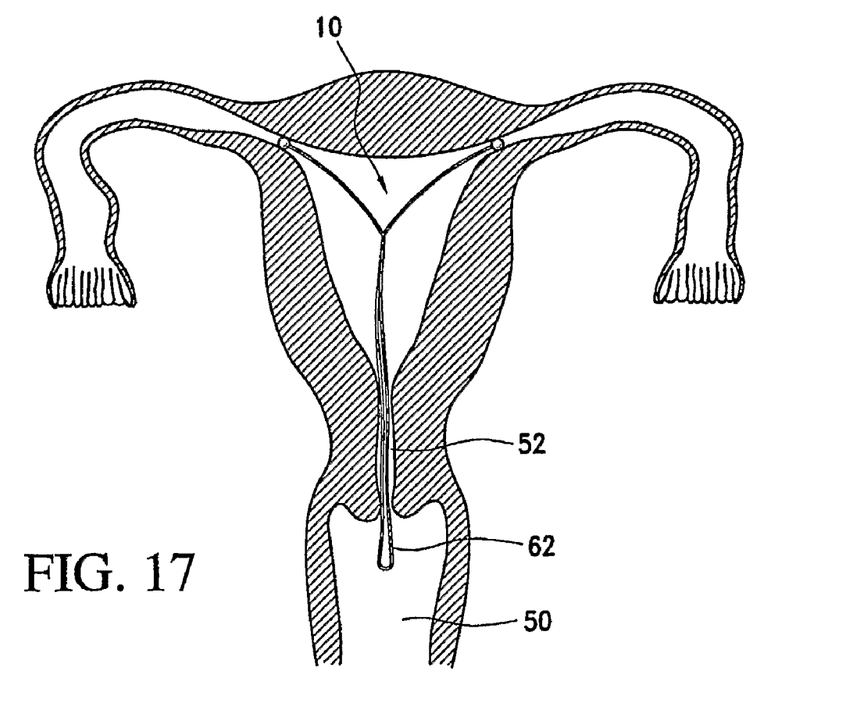

As those skilled in the art will appreciate, other removal techniques are contemplated in accordance with the present invention. For example, and with reference to FIGS. 16 and 17 another removal method would be by leaving a string 60 or loop 62 attached to the occlusion device 10. The string 60 or loop 62 is left protruding out of the cervix 52 and into the vagina 50 for easy removal thereof. This string 60 or loop 62 can be pulled in the office and the occlusion device 10 removed. Alternatively, the string can be connected to a removal device that will pull the occlusion device back into the sheath.

The novelty of the present device is that in addition to being an intrauterine device it will actively occlude the fallopian tubes. This occlusion will prevent sperm or other material from migrating from the uterus to the fallopian tubes and vice versa.

The present device offers a variety of other uses. These uses include applications for contraception, either temporary of permanent; especially for women who do not use IUDs because of the "post fertilization-embryo destruction" method of contraception. The present occlusion device may also be used by women who do not wish to undergo a tubal ligation surgery.

The present occlusion device may potentially also be used in the treatment of endometriosis. Back flush of menstrual blood through the fallopian tubes is a proposed mechanism for this disease. The present occlusion device will allow occlusion of the fallopian tubes as a possible treatment. Endometriosis is usually affecting younger patients and other methods of tubal ligation or occlusion are not warranted.

Although a preferred embodiment disclosed above shows the orifice plugs as being permanently coupled to the ends of the resilient body, the resilient body, delivery rod and container may serve as a delivery system of the orifice plugs to the orifices of the fallopian tubes. More particular, and with reference to FIGS. 18, 19 and 20, the concepts underlying the present invention are utilized in conjunction with the shape of the uterine cavity 16 to conform the first and second orifice plugs 120, 122 of the occlusion device 110 in the orifices 12 of the fallopian tubes 14. As with the prior embodiments, the orifice plugs 120, 122 may contain any kind of material or medicine to be delivered into the orifices 12 or the fallopian tubes 14.

Figure 18:
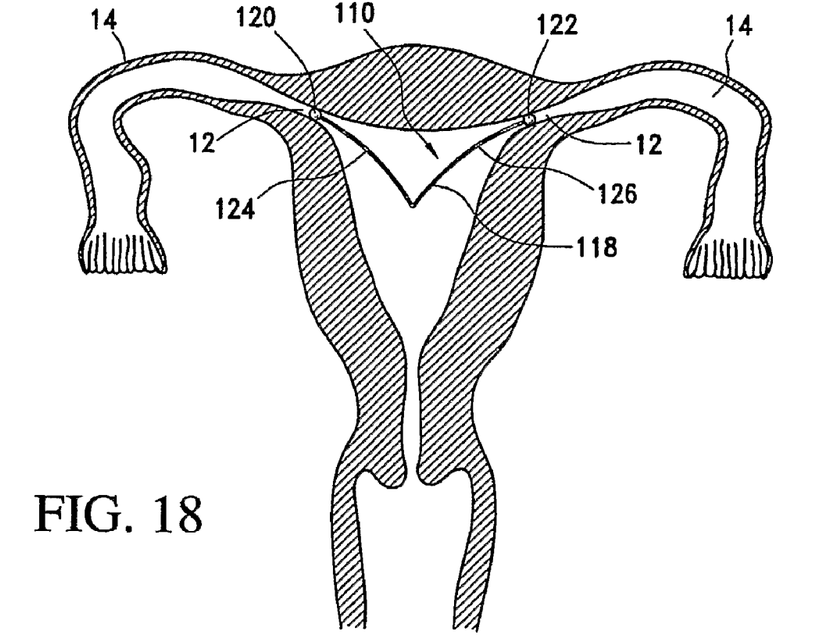
FIGS. 18, 19 and 20 are various views showing delivery of an alternate embodiment in which the orifice plugs are selectively detachable from the resilient body.
Figure 19:
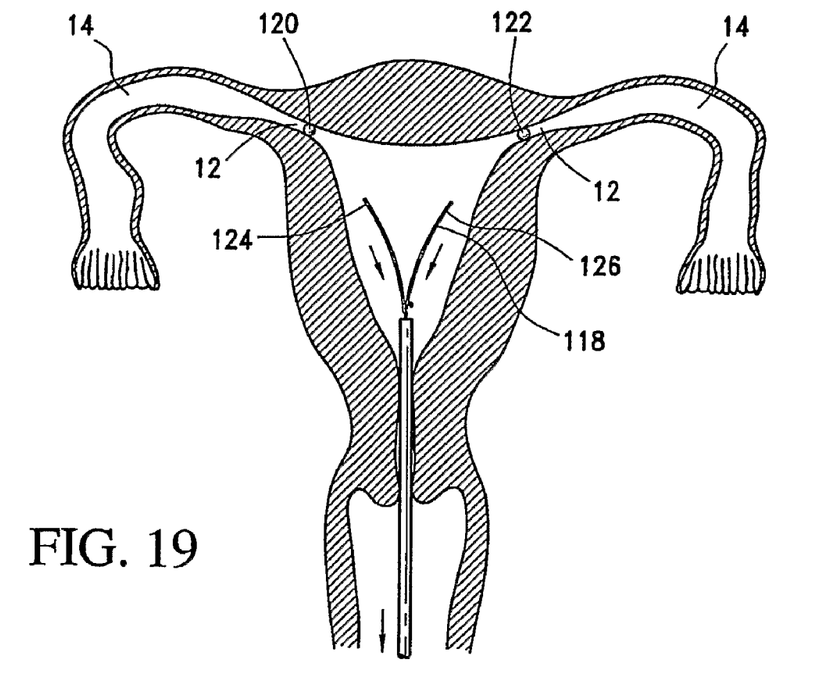
Figure 20:
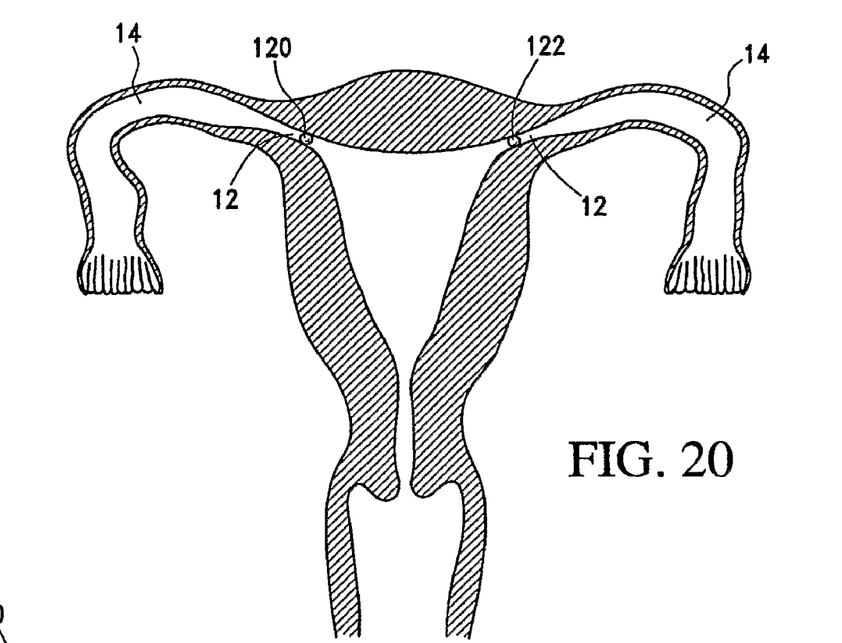

The orifice plugs 120, 122 are releasably secured to the first and second ends 124, 126 of the resilient body 118 and, therefore, may be left in place by separating them from the resilient body 118. As those skilled in the art will certainly appreciate a variety of methods for separation of the orifice plugs 120, 122 with the resilient body 118 may be employed within the spirit of the present invention. For example, release may be achieved by mechanically coupling mechanisms or heat activated release mechanism wherein a coupling structure melts or separates the connection or connections between the plugs and the resilient body when the device is placed within the body (either immediately or over time and hence separate the plugs from the delivery device).

Figure 21:
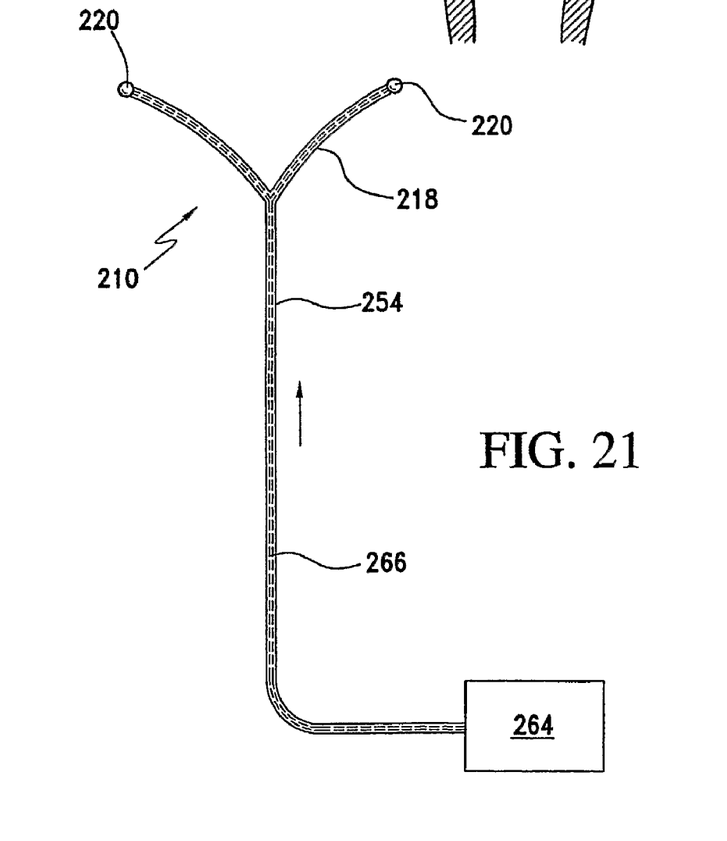
FIG. 21 is a front view of an occlusion device in accordance with yet a further embodiment of the present invention.
Figure 22:
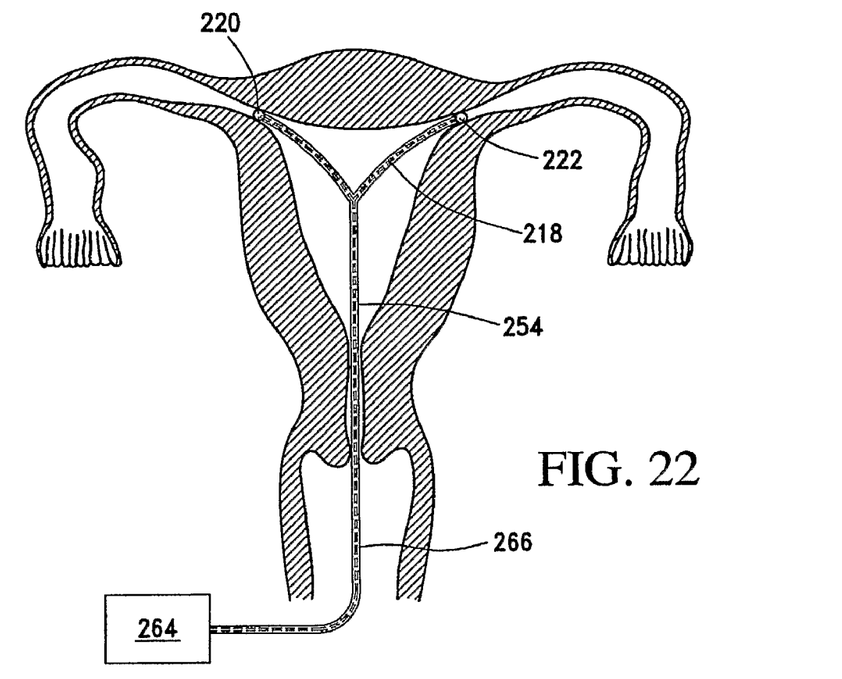
FIGS. 22 and 23 show delivery of the occlusion device shown in FIG. 21.
Figure 23:
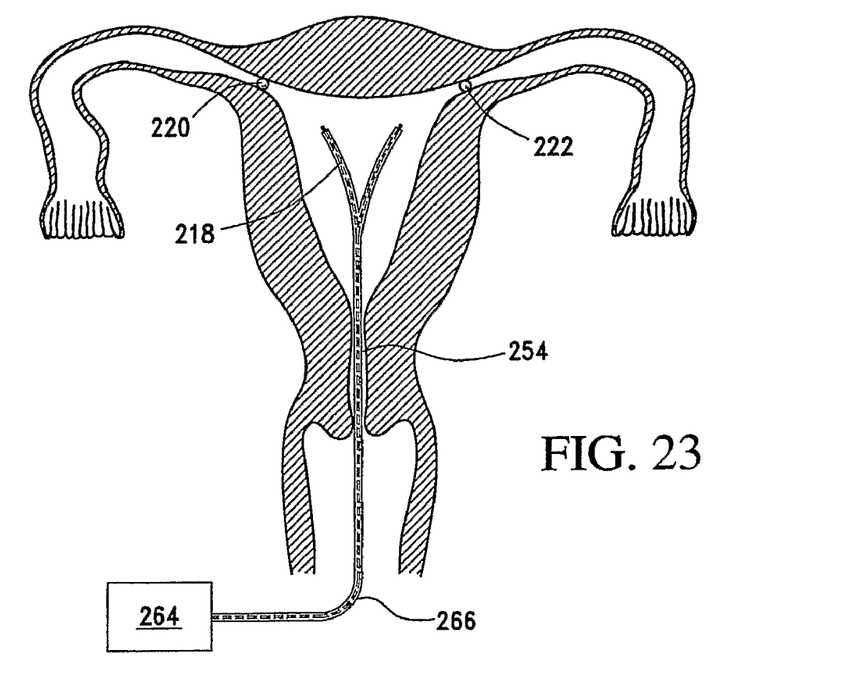

In accordance with an alternate embodiment and with reference to FIGS. 21, 22 and 23, the occlusion device 210 is provided with an energy source 264 (for example, electrical energy source or RF energy source) is linked to the orifice plugs 220, 222 in a manner incorporating the orifice plugs 220, 222 into the tissue at the orifices 12 of the fallopian tubes 14. More particular, a wire 266 extends through the delivery rod 254 and resilient body 218, and into the first and second orifice plugs 220, 222. The energy from the energy source 264 may, therefore, be selectively transferred from the energy source 264 to the orifice plugs 220, 222 in a manner facilitating the incorporation of the orifice plugs 220, 222 into the adjacent tissue. In order to ensure transfer of the energy to the tissue, the orifice plugs 220 are made of a conductive material designed to receive and transmit the energy received from the energy source 264.

As with the embodiment disclosed with reference to FIGS. 18, 19 and 20, the first and second orifice plugs 220, 222 are selectively detachable from the resilient body 218 in accordance with a preferred embodiment of the present invention. However, and as those skilled in the art will certainly appreciate, the orifice plugs may be fixedly secured to the resilient body without departing from the spirit of the present invention.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. An occlusion device for actively occluding the orifices of the fallopian tubes using the shape of the uterine cavity as a guide to proper positioning of the occlusion device, the occlusion device comprising:
    a resilient body including an elongated member having a first end and second end;
    a first orifice plug secured at the first end of the elongated member and a second orifice plug secured at the second end of the elongated member;
    the first end of the elongated member is composed of a first leg and the second end of the elongated member is composed of a second leg, and wherein the first leg includes a first end and second end, and the second leg includes a first end and second end, and the first ends of the respective first and second legs are respectively connected by a connection, while the second ends of the first and second legs are respectively free and are provided with the respective first and second orifice plugs, the first leg and the second leg are angularly oriented relative to each other such that the elongated member is substantially V-shaped when the first leg and the second leg are allowed to move away from each other based upon the outward bias inherent in the connection and the resilience of the first leg and the second leg causing an outward bow in the first leg and the second leg when they are unrestrained, the first leg and the second leg forming a maximum angle of approximately 150 degrees relative to each other when entirely unrestrained;
    wherein the first and second orifice plugs are shaped and dimensioned to seat at the orifices of the fallopian tubes or within the fallopian tubes as the elongated member spreads outwardly with the first end and second end moving apart until the first and second orifice plugs of the occlusion device distally reach respective walls of the uterine cavity, ride up the walls of the uterine cavity and seat at the orifices of the fallopian tubes or within the fallopian tubes.

2. The occlusion device according to claim 1, wherein the elongated body is made of a shape memory alloy.

3. The occlusion device according to claim 2, wherein the elongated body is made of Nitinol.

4. The occlusion device according to claim 2, wherein the first and second orifice plugs are made from silicone, metal, plastic or mesh.

5. The occlusion device according to claim 1, wherein the elongated member and the first and second orifice plugs are inert.

6. The occlusion device according to claim 1, wherein the elongated member or the first and second orifice plugs are treated with an active substance.

7. The occlusion device according to claim 1, further including an energy source coupled to the first and second orifice plugs.

8. The occlusion device according to claim 1, wherein the first and second orifice plugs are detachably secured to the elongated member.

9. A method for occluding the fallopian tubes, comprising the following steps:
    delivering an occlusion device into the uterine cavity through the vagina and cervix, the occlusion device including a resilient body having an elongated member with a first end and second end, and a first orifice plug secured at the first end of the elongated member and a second orifice plug secured at the second end of the elongated member, wherein the first and second orifice plugs are shaped and dimensioned to seat at the orifices of the fallopian tubes or within the fallopian tubes as the elongated member spreads outwardly with the first end and second end moving apart;
    releasing the occlusion device and allowing the first end and the second end of the elongated member to move apart until the first and second orifice plugs of the occlusion device distally reach the wall of the uterine cavity and ride up the walls of the uterine cavity until the first and second orifice plugs seat at the orifices of the fallopian tubes or within the fallopian tubes;
    wherein the first and second orifice plugs are detachably secured to the elongated member.

* * * * *